United States Patent
Yoshida

(10) Patent No.: US 10,249,419 B2
(45) Date of Patent: Apr. 2, 2019

(54) SUPERCONDUCTIVE ELECTROMAGNET AND CHARGED PARTICLE BEAM THERAPY APPARATUS

(71) Applicant: Sumitomo Heavy Industries, Ltd., Tokyo (JP)

(72) Inventor: Jun Yoshida, Kanagawa (JP)

(73) Assignee: SUMITOMO HEAVY INDUSTRIES, LTD., Tokyo (JP)

(*) Notice: Subject to any disclaimer, the term of this patent is extended or adjusted under 35 U.S.C. 154(b) by 423 days.

(21) Appl. No.: 14/716,400

(22) Filed: May 19, 2015

(65) Prior Publication Data
US 2015/0340140 A1   Nov. 26, 2015

(30) Foreign Application Priority Data
May 20, 2014   (JP) ................ 2014-104485

(51) Int. Cl.
| H01F 1/00 | (2006.01) |
| H01F 6/06 | (2006.01) |
| H01F 6/00 | (2006.01) |
| A61N 5/10 | (2006.01) |
| H05H 7/04 | (2006.01) |

(52) U.S. Cl.
CPC ............ *H01F 6/06* (2013.01); *A61N 5/1043* (2013.01); *H01F 6/00* (2013.01); *H05H 7/04* (2013.01); *A61N 2005/1087* (2013.01); *H05H 2007/046* (2013.01)

(58) Field of Classification Search
CPC ..... H05H 7/04–2007/048; H01J 23/087; H01J 23/10; H01F 6/06
USPC ........................................ 335/261
See application file for complete search history.

(56) References Cited

U.S. PATENT DOCUMENTS

| 5,410,287 A * | 4/1995 | Laskaris ............ G01R 33/3806 324/318 |
| 5,485,088 A * | 1/1996 | Westphal ............ G01R 33/387 324/319 |
| 5,521,571 A * | 5/1996 | Laskaris ............ G01R 33/3806 324/320 |
| 5,545,997 A * | 8/1996 | Westphal ............ G01R 33/3815 324/319 |

(Continued)

FOREIGN PATENT DOCUMENTS

| JP | 2010-287792 A | 12/2010 |
| JP | 2011-072717 A | 4/2011 |

*Primary Examiner* — Shawki S Ismail
*Assistant Examiner* — Lisa N Homza
(74) *Attorney, Agent, or Firm* — Michael Best & Friedrich LLP

(57) ABSTRACT

A superconductive electromagnet according to an embodiment includes a pair of main coils that have an annular shape, a pair of magnetic poles that are arranged on an inner peripheral side of the main coils, and that respectively have opposing surfaces which are planes opposing each other while being separated from each other in an axial direction of the main coils, and a pair of correction coils that are arranged between a pair of the magnetic poles. In this manner, density of a magnetic flux generated by the main coils is corrected by density of a magnetic flux generated by the correction coils. Accordingly, it is possible to realize improved uniformity in the density of the magnetic flux in a beam duct inside a deflection electromagnet.

7 Claims, 7 Drawing Sheets

(56) References Cited

U.S. PATENT DOCUMENTS

| | | | | |
|---|---|---|---|---|
| 5,568,110 A * | 10/1996 | Dorri | ................. | G01R 33/3815 |
| | | | | 324/319 |
| 5,574,417 A * | 11/1996 | Dorri | ................. | G01R 33/3806 |
| | | | | 324/319 |
| 5,594,401 A * | 1/1997 | Dorri | ................. | G01R 33/3815 |
| | | | | 324/319 |
| 5,600,245 A * | 2/1997 | Yamamoto | ........... | G01R 33/385 |
| | | | | 324/318 |
| 5,625,331 A * | 4/1997 | Yamada | ................... | H05H 7/04 |
| | | | | 335/210 |
| 5,721,523 A * | 2/1998 | Dorri | ................. | G01R 33/3806 |
| | | | | 324/319 |
| 6,100,780 A * | 8/2000 | Dorri | ................. | G01R 33/3806 |
| | | | | 335/216 |
| 7,414,401 B1 * | 8/2008 | Lvovsky | ............ | G01R 33/3875 |
| | | | | 324/309 |
| 7,812,319 B2 * | 10/2010 | Diehl | .................... | G21K 1/093 |
| | | | | 250/396 ML |
| 2004/0041673 A1 * | 3/2004 | Kakugawa | ......... | G01R 33/3806 |
| | | | | 335/299 |
| 2005/0068139 A1 * | 3/2005 | Abe | ................... | G01R 33/3806 |
| | | | | 335/300 |
| 2006/0001427 A1 * | 1/2006 | Ando | ................. | G01R 33/3873 |
| | | | | 324/320 |
| 2009/0101832 A1 * | 4/2009 | Diehl | ................... | A61N 5/1043 |
| | | | | 250/398 |

* cited by examiner

SUPERCONDUCTIVE ELECTROMAGNET AND CHARGED PARTICLE BEAM THERAPY APPARATUS

RELATED APPLICATIONS

Priority is claimed to Japanese Patent Application No. 2014-104485, filed May 20, 2014, the entire content of which is incorporated herein by reference.

BACKGROUND

Technical Field

Certain embodiments of the invention relate to a superconductive electromagnet and a charged particle beam therapy apparatus.

Description of Related Art

For example, a beam transport line for transporting a charged particle beam in the related art deflects the charged particle beam by causing a deflection electromagnet to generate a magnetic field in a beam duct through which the charged particle beam passes. In this case, it is necessary to allow uniform density of a magnetic flux in the beam duct inside the deflection electromagnet in order to accurately deflect the charged particle beam. Here, the related art discloses that a superconductive electromagnet is used as an electromagnet of the beam transport line in order to miniaturize the electromagnet while allowing the uniform density of the magnetic flux.

However, the superconductive electromagnet has a strong magnetomotive force. Consequently, in some cases, a magnetic pole arranged inside the electromagnet causes magnetic saturation. In this case, the density of the magnetic flux between magnetic poles becomes high particularly in the vicinity of a center position of the electromagnet, thereby degrading uniformity. In contrast, for example, it is also conceivable to realize uniform density of the magnetic flux is obtained by forming an irregular shape on an opposing surface of the magnetic pole. However, according to this method, an advantageous effect can be obtained for only the density of the magnetic flux having a specific size. Therefore, if the size varies in the density of the magnetic flux, the uniformity cannot be maintained.

It is desirable to provide a superconductive electromagnet and a charged particle beam therapy apparatus which can realize improved uniformity in density of a magnetic flux between magnetic poles.

SUMMARY

According to an embodiment of the invention, there is provided a main coil that has an annular shape, a pair of magnetic poles that respectively have opposing surfaces which are planes opposing each other while being separated from each other in an axial direction of the main coil, and that are arranged on an inner peripheral side of the main coil, and a correction coil that is arranged between a pair of the magnetic poles.

A charged particle beam therapy apparatus according to another embodiment of the invention has the above-described superconductive electromagnet.

DETAILED DESCRIPTION

Figure 1:
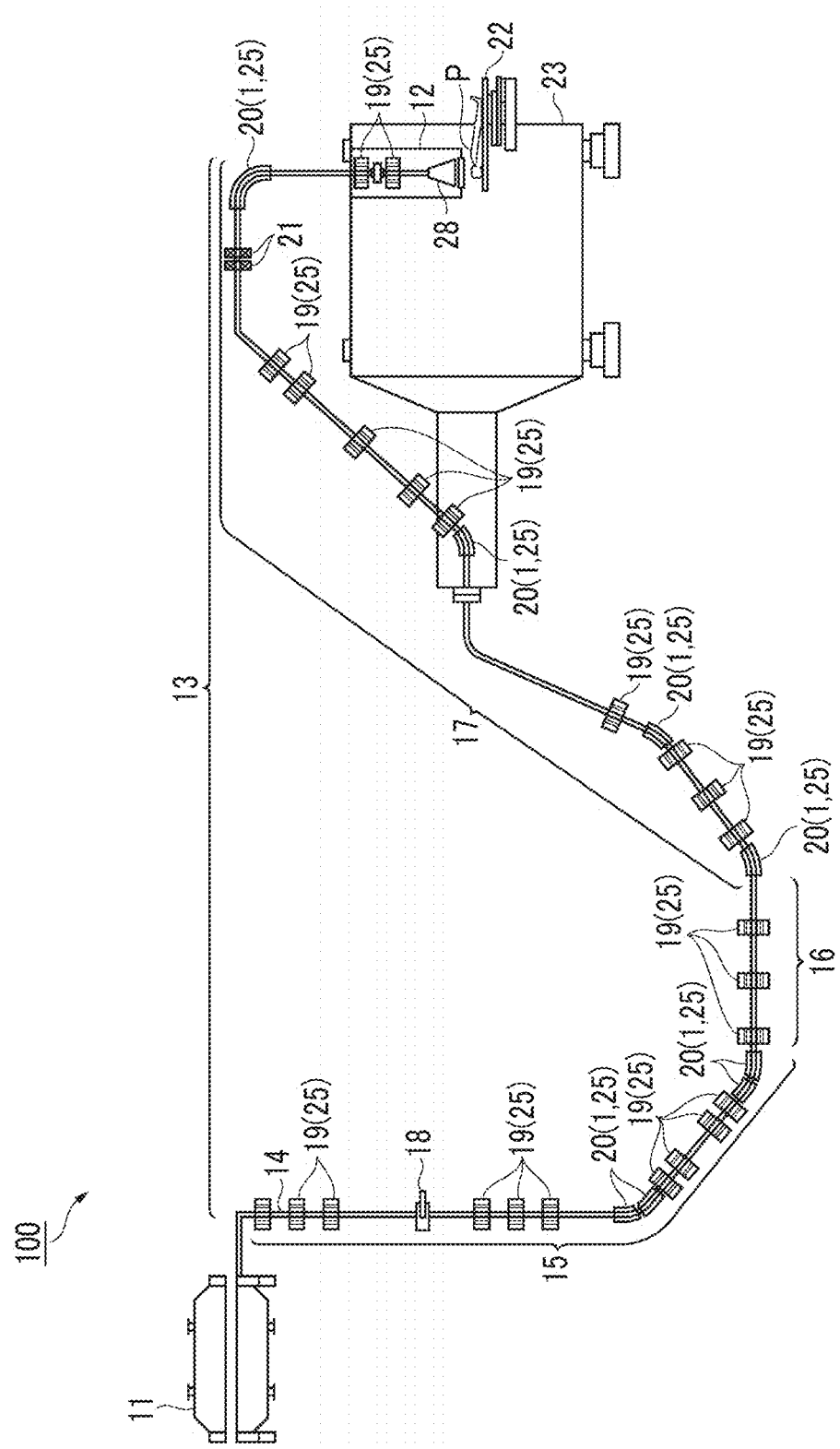
FIG. 1 is a schematic view illustrating an embodiment of a charged particle beam therapy apparatus.

In the superconductive electromagnet according to an embodiment of the invention, the correction coil is arranged between a pair of the magnetic poles on the inner peripheral side of the main coil having an annular shape. In this manner, density of a magnetic flux generated by the main coil is corrected by density of a magnetic flux generated by the correction coil. Accordingly, it is possible to realize improved uniformity in the density of the magnetic flux between the magnetic poles. That is, it is possible to realize improved uniformity in the density of the magnetic flux between the magnetic poles in a state where the superconductive electromagnet is enabled to cope with a change in the density of the magnetic flux covering a wide range by configuring the opposing surface of the respective magnetic poles so as to be a plane.

The superconductive electromagnet according to the embodiment of the invention may further include at least a pair of the correction coils. In this manner, it is possible to realize more improved uniformity in the density of the magnetic flux between the magnetic poles.

In the superconductive electromagnet according to the embodiment of the invention, the correction coil may be configured so that a width in the axial direction of the correction coil is narrower than a width in a direction orthogonal to the axial direction of the correction coil, in a cross section perpendicular to a current flowing direction. In this manner, the density of the magnetic flux generated by the correction coil can be concentrated on a narrow region. Therefore, it is possible to efficiently realize improved uniformity in the density of the magnetic flux between the magnetic poles.

The superconductive electromagnet according to the embodiment of the invention may further include a support unit that supports the main coil and supports the correction coil. In this manner, it is possible to support the correction coil and to reinforce the main coil. Therefore, it is possible to prevent the main coil from being deformed due to an extending force acting so as to extend the main coil outward.

In this manner, density of a magnetic flux generated by the main coil is corrected by density of a magnetic flux generated by the correction coil. Therefore, it is possible to realize improved uniformity in the density of the magnetic flux between the magnetic poles.

The charged particle beam therapy apparatus according to the embodiment of the invention may further include a deflection electromagnet that deflects a charged particle beam and a scanning electromagnet that performs scanning by using the charged particle beam. The above-described superconductive electromagnet may be used as the deflection electromagnet which is disposed on a further downstream side of the charged particle beam from the scanning electromagnet. In this manner, even if the superconductive electromagnet is used as the deflection electromagnet which is disposed on a downstream side of the scanning electromagnet, it is possible to realize improved uniformity in the density of the magnetic flux between the magnetic poles of the deflection electromagnet.

Hereinafter, embodiments according to the invention will be described in detail with reference to the drawings. Terms of "upstream" and "downstream" respectively mean an upstream side (accelerator side) and a downstream side (patient side) of an emitted charged particle beam.

As illustrated in FIG. 1, a charged particle beam therapy apparatus 100 is an apparatus used for cancer therapy using radiotherapy, and includes an accelerator 11 which accelerates a charged particle beam so as to emit a charge particle beam, an irradiation nozzle 12 which irradiates an irradiation target with the charged particle beam, a beam transport line 13 which transports the charged particle beam emitted from the accelerator 11 to the irradiation nozzle 12, a degrader 18 which is disposed in the beam transport line 13 and degrades energy of the charged particle beam so as to adjust a range of the charged particle beam, and multiple electromagnets 25 which are disposed in the irradiation nozzle 12 and the beam transport line 13. The embodiment described herein employs a cyclotron as the accelerator 11. However, without being limited thereto, the embodiment may employ other generation sources for generating the charged particle beam, such as a synchrotron, a synchrocyclotron, and a linear accelerator, for example.

The charged particle beam therapy apparatus 100 irradiates a tumor (irradiation target) of a patient P lying on a therapy bed 22 with the charged particle beam emitted from the accelerator 11. The charged particle beam is obtained by accelerating a particle having a charge at high speed, and is a proton beam or a heavy particle (heavy ion) beam. The charged particle beam therapy apparatus 100 according to the embodiment described herein performs irradiation of the charged particle beam by means of a so-called scanning method, and virtually divides (slices) the irradiation target in a depth direction so as to irradiate every slice plane (layer) in an irradiation range on the layer with the charged particle beam.

For example, an irradiation method using the scanning method includes spot-type scanning irradiation and a raster-type scanning irradiation. The spot-type scanning irradiation is a method in which beam (charged particle beam) irradiation is stopped once if irradiation is completed for one spot in the irradiation range, and irradiation is performed for the subsequent spot after the irradiation is well prepared for the subsequent spot. In contrast, the raster-type scanning irradiation is a method in which the irradiation is not intermitted for the irradiation range on the same layer, and the beam irradiation is continuously performed. In this way, according the raster-type scanning irradiation, the beam irradiation is continuously performed for the irradiation range on the same layer. Therefore, unlike the spot-type scanning irradiation, the irradiation range is not configured to include multiple spots.

The irradiation nozzle 12 is attached to an inner side of a rotary gantry 23 which can rotate around the therapy bed 22 by 360 degrees, and is adapted to be movable to any desired rotation position by the rotary gantry 23. The irradiation nozzle 12 includes a focusing electromagnet 19 and a beam duct 28.

The beam transport line 13 has a beam duct 14 through which the charged particle beam passes. The beam duct 14 internally maintains a vacuum state, thereby preventing a charged particle configuring the charged particle beam from being scattered by air or the like during transportation.

The beam transport line 13 has an energy selection system (ESS) 15 which selectively extracts the charged particle beam having an energy width narrower than a predetermined energy width from the charged particle beams emitted from the accelerator 11 and having the predetermined energy width, a beam transport system (BTS) 16 which transports the charged particle beam having the energy width selected by the ESS 15 in a state where energy is maintained, and a gantry transport system (GTS) 17 which transports the charged particle beam from the BTS 16 toward the rotary gantry 23.

The degrader 18 degrades the energy of the charged particle beam passing therethrough so as to adjust a range of the charged particle beam. A depth from a body surface of the patient P to the tumor of the irradiation target varies depending on each patient P. Accordingly, when the patient P is irradiated with the charged particle beam, it is necessary to adjust the range which represents a reachable depth of the charged particle beam. The degrader 18 adjusts the energy of the charged particle beam emitted from the accelerator 11 with constant energy, thereby adjusting the charged particle beam so as to properly reach the irradiation target located at a predetermined depth inside the body of the patient P. This energy adjustment of the charged particle beam is performed by the degrader 18 for every sliced layer of the irradiation target.

The electromagnet 25 is disposed at multiple locations of the beam transport line 13, and adjusts the charged particle beam so that a magnetic field enables the charged particle beam to be transported by using the beam transport line 13. The electromagnet 25 employs the focusing electromagnet 19 which focuses a beam diameter of the charged particle beam during the transportation, a scanning electromagnet 21 which performs scanning by using the charged particle beam, and a deflection electromagnet 20 (to be described in detail later) which deflects the charged particle beam configured to include a superconductive electromagnet 1 according to the embodiment described herein. In the following description, in some cases, the focusing electromagnet 19, the deflection electromagnet 20, and the scanning electromagnet 21 will be described as the electromagnet 25 without particular distinction therebetween. In addition, the electromagnet 25 is disposed at multiple locations on a further downstream side from the degrader 18 within at least the beam transport line 13. However, in the embodiment described herein, the electromagnet 25 is also disposed on a further upstream side from the degrader 18. Here, the focusing electromagnet 19 serving as the electromagnet 25 is also disposed on the upstream side of the degrader 18 in order to focus the beam diameter of the charged particle beam before the energy is adjusted by the degrader 18. A total number of the electromagnets 25 can be flexibly changed depending on a length of the beam transport line 13, and is set to approximately 10 to 40, for example.

The scanning electromagnet 21 has an X-direction scanning electromagnet which performs scanning in an X-direction by using the charged particle beam on a plane intersecting a travelling direction of the charged particle beam, and a Y-direction scanning electromagnet which performs scanning in a Y-direction intersecting the X-direction by using the charged particle beam on a plane intersecting the travelling direction of the charged particle beam. In addition, the charged particle beam used for the scanning by the scanning electromagnet 21 is deflected in the X-direction and/or in the Y-direction. Accordingly, the beam duct 14 located on the further downstream side from the scanning electromagnet 21 has a diameter which expands toward the downstream side.

A position of the degrader 18 and the electromagnet 25 within the beam transport line 13 is not particularly limited. According to the embodiment described herein, the degrader 18, the focusing electromagnet 19, and the deflection electromagnet 20 are disposed in the ESS 15. The focusing electromagnet 19 is disposed in the BTS 16. The focusing electromagnet 19, the deflection electromagnet 20, and the scanning electromagnet 21 are disposed in the GTS 17. However, the position of the scanning electromagnet 21 may be different from the position illustrated in FIG. 1. For example, the scanning electromagnet 21 may be arranged between the focusing electromagnet 19 of the irradiation nozzle 12 and the beam duct 28. As described above, the degrader 18 is arranged in the ESS 15 located between the accelerator 11 and the rotary gantry 23. More specifically, the degrader 18 is disposed on the accelerator 11 side (upstream side) rather than the rotary gantry 23 within the ESS 15.

Subsequently, the deflection electromagnet 20 configured to include the superconductive electromagnet 1 according to the embodiment described herein will be described in detail.

Figure 2:
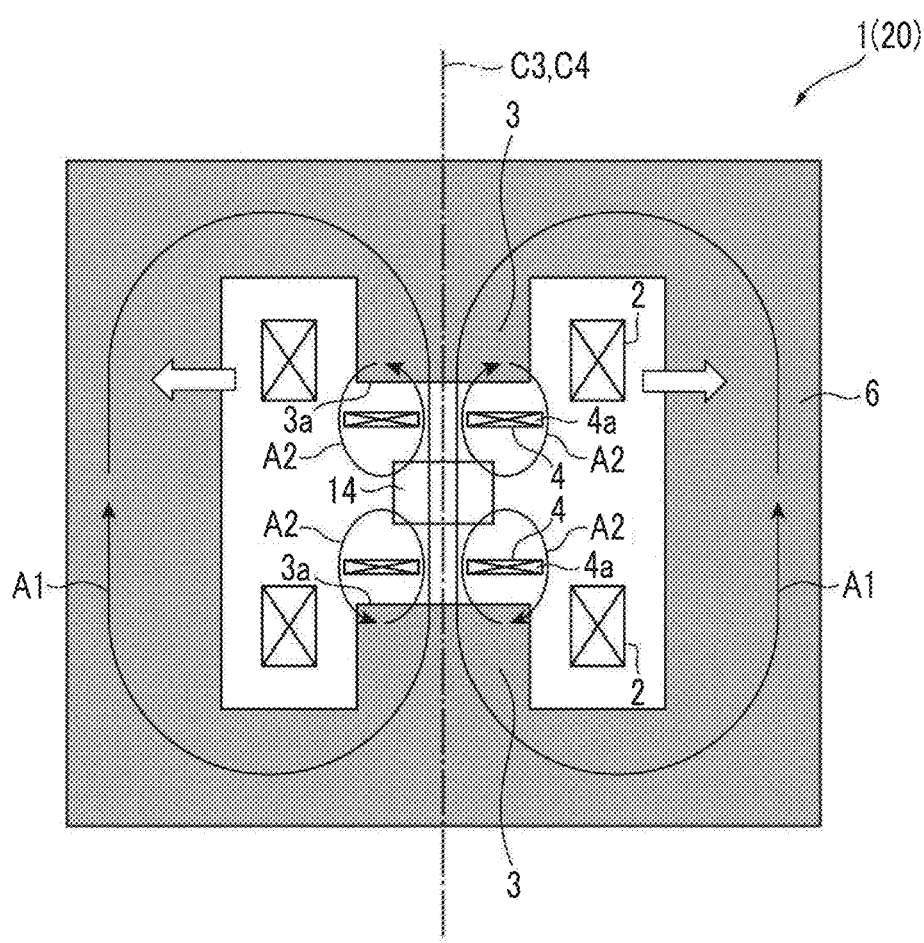
FIG. 2 is a schematic view illustrating an embodiment of a superconductive electromagnet.
Figure 3:
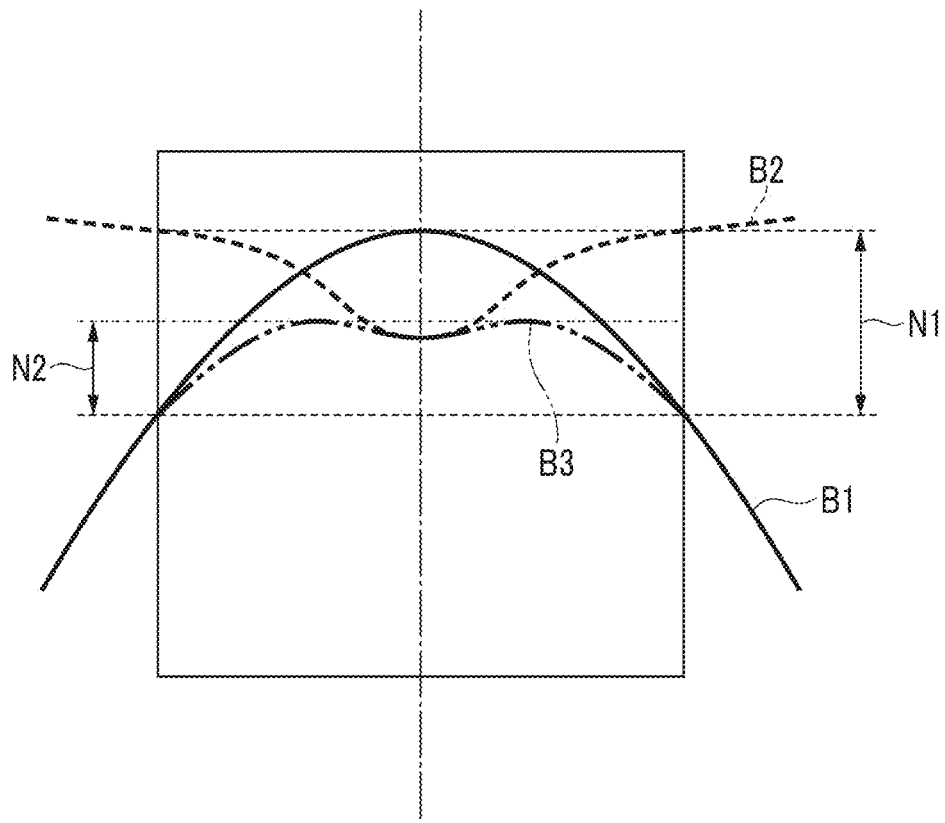
FIG. 3 is a schematic view illustrating density of a magnetic flux in a beam duct.

Referring to FIGS. 2 and 3, description will be made with regard to the deflection electromagnet 20 which is configured to include the superconductive electromagnet 1 according to the embodiment described herein and which deflects the charged particle beam. The deflection electromagnet 20 is configured to include the superconductive electromagnet 1 in order to increase a magnetomotive force. As illustrated in FIG. 2, the deflection electromagnet 20 has a pair of main coils 2 and 2 having an annular shape, a pair of magnetic poles 3 and 3 which are arranged on an inner peripheral side of the main coil 2, a pair of correction coils 4 and 4 which are arranged between a pair of the magnetic poles 3 and 3 and have an annular shape, and the beam duct 14 which is disposed between a pair of the correction coils 4 and 4 so as to pass through the deflection electromagnet 20. In addition, the deflection electromagnet 20 includes a support unit 5 which supports the main coil 2 and supports the correction coil 4 (refer to FIGS. 4 and 5). The correction coil 4 is arranged in a direction where an axis C4 of the correction coil 4 is substantially parallel to an axis C3 of the main coil 2. A planar shape of the main coil 2 and the correction coil 4 is not particularly limited, and may be a semicircular shape, for example. Accordingly, the axes C3 and C4 indicate center lines in only a cross section illustrated in FIG. 2. FIG. 2 illustrates the axis C3 of the main coil 2 and the axis C4 of the correction coil 4 so as to overlap each other. The main coil 2 and the correction coil 4 are arranged in the same cryogenic container (not illustrated). In addition, the main coil 2 and the correction coil 4 are mechanically and thermally connected to each other through a portion between the magnetic pole 3 and the beam transport line 13. A pair of the magnetic poles 3 and 3 respectively have opposing surfaces 3a and 3a which are planes opposing each other while being separated from each other in a direction of the axis C3 of the main coil 2. In addition, a pair of the magnetic poles 3 and 3 are formed integrally with a yoke 6 formed so as to surround the main coil 2. In the deflection electromagnet 20, the flat correction coil 4 (to be described later) is arranged in a gap by lengthening a distance of the gap between the opposing surfaces 3a and 3a of a pair of magnetic poles 3 and 3.

The main coil 2 is formed by using a superconductive coil, and is formed by using a high-temperature superconductive coil suitable for fast demagnetization. The high-temperature superconductive coil is suitable for the fast demagnetization since the high-temperature superconductive coil has a high critical temperature and is likely to maintain a superconductive state even when heat is generated due to the fast demagnetization. The main coil 2 generates a magnetic field around itself if power is supplied thereto from an electromagnet power source (not illustrated). For example, as illustrated by an arrow A1, the magnetic field generated by the main coil 2 passes through the inner peripheral side of the correction coil 4 and the beam duct 14 by way of one magnetic pole 3 from the yoke 6. Furthermore, the magnetic field returns to the yoke 6 byway of the other magnetic pole 3, thereby forming a magnetic circuit.

The correction coil 4 has a cross-sectional flat shape. That is, as illustrated in FIG. 2, the correction coil 4 is formed so that a width in the direction of the axis C4 of the correction coil 4 is narrower than a width in the direction orthogonal to the direction of the axis C4 of the correction coil 4 in a cross section 4a perpendicular to a current flowing direction. One correction coil 4 is disposed between the beam duct 14 and one magnetic pole 3. In addition, the other correction coil 4 is disposed between the beam duct 14 and the other magnetic pole 3. The correction coils 4 and 4 are respectively arranged on the inner peripheral side of the main coils 2 and 2. In the embodiment described herein, the correction coils 4 and 4 are arranged at a position of opposing the opposing surfaces 3a and 3a of the magnetic poles 3 and 3 (that is, position where at least a portion of the correction coil 4 overlaps the opposing surface 3a when viewed in a direction along the axis C3 (or the axis C4)). However, a position and a size of the correction coils 4 and 4 are not particularly limited as long as the main coils 2 and 2 can correct density of a magnetic flux. In addition, the correction coil 4 is formed by using a superconductive coil similarly to the main coil 2. In particular, the correction coil 4 is formed by using a high-temperature superconductive coil suitable for fast demagnetization. The correction coil 4 generates a magnetic field around itself by the power being supplied thereto from another electromagnet power source (not illustrated) which is different from the electromagnet power source (not illustrated) for supplying the power to the main coil 2. The electromagnet power sources for supplying the power to the main coil 2 and the correction coil 4 are different from each other. Accordingly, even if the main coil 2 changes a size of density of a magnetic flux, the correction coil 4 adjusts the size of density of the magnetic flux. In this manner, it is possible to maintain uniform density of the magnetic flux in the beam duct 14 inside the deflection electromagnet 20.

For example, as illustrated by an arrow A2, a magnetic field generated by the correction coil 4 forms a magnetic circuit around the correction coil 4. As illustrated in FIG. 3, the density of the magnetic flux generated by the correction coil 4 is added to the density of the magnetic flux generated by the main coil 2, thereby correcting distribution of the density of the magnetic flux in the beam duct 14 inside the deflection electromagnet 20. In FIG. 3, density B1 of a magnetic flux generated by the main coil 2 is illustrated by a solid line, density B2 of a magnetic flux generated by the correction coil 4 is illustrated by a dashed line, and density B3 of a magnetic flux which is corrected by using the density B2 of the magnetic flux is illustrated by a two-dot chain line. As illustrated in FIG. 3, as compared to a non-uniform width N1 of the density B1 of the magnetic flux generated by the main coil 2 in a range surrounded by a square, a non-uniform width N2 of the density B3 of the magnetic flux after being corrected by using the density B2 of the magnetic flux generated by the correction coil 4 in a range surrounded by a square is narrower. That is, the density of the magnetic flux in the beam duct 14 is corrected, thereby improving uniformity. In the embodiment described herein, the direction of the axis C4 of the correction coil 4 is substantially parallel to the direction of the axis C3 of the main coil 2, and the power is supplied to the main coil 2 and the correction coil 4 so that currents reversely flow around both of these. In this manner, in order to negate the density of the magnetic flux near the axis C3 of the main coil 2 which becomes particularly high due to magnetic saturation of the magnetic pole 3 within the density of the magnetic flux generated by the main coil 2, the correction coil 4 generates a magnetic field so that the density of the magnetic flux becomes high in a narrow range near the axis C4.

Figure 4:
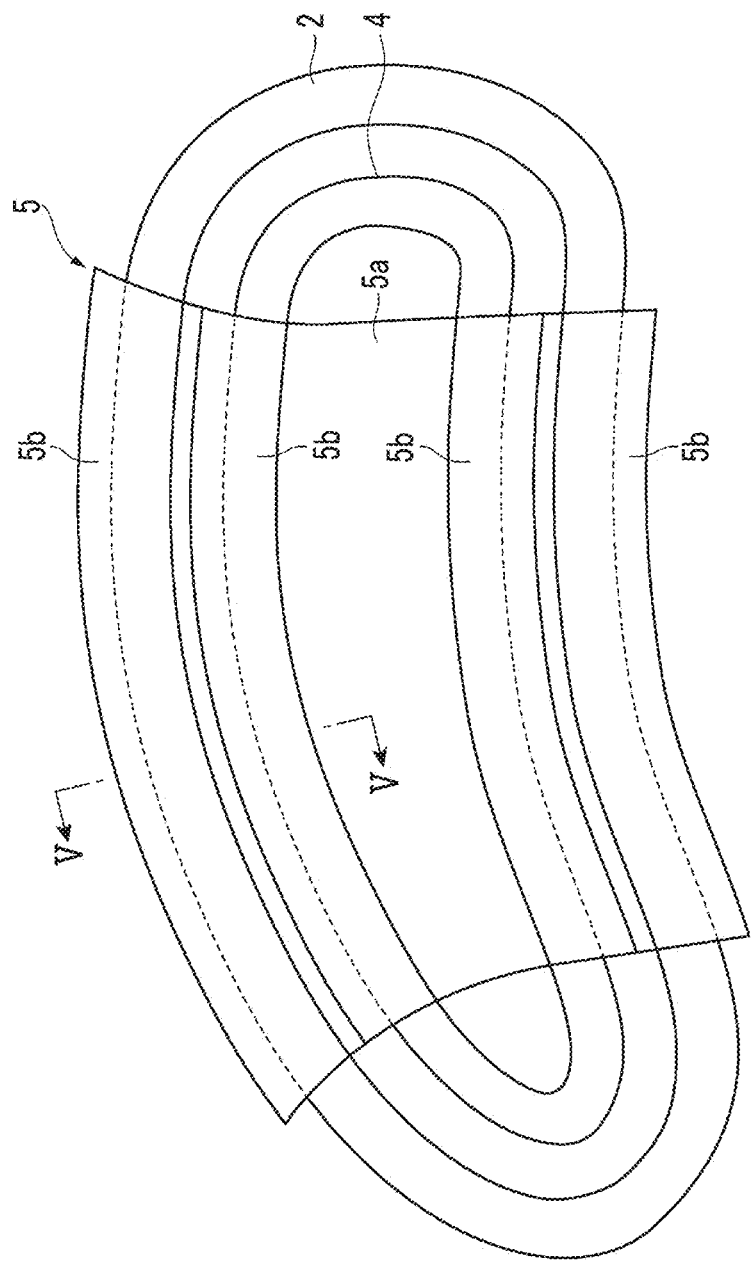
FIG. 4 is a schematic view illustrating a planar shape of a support unit.
Figure 5:
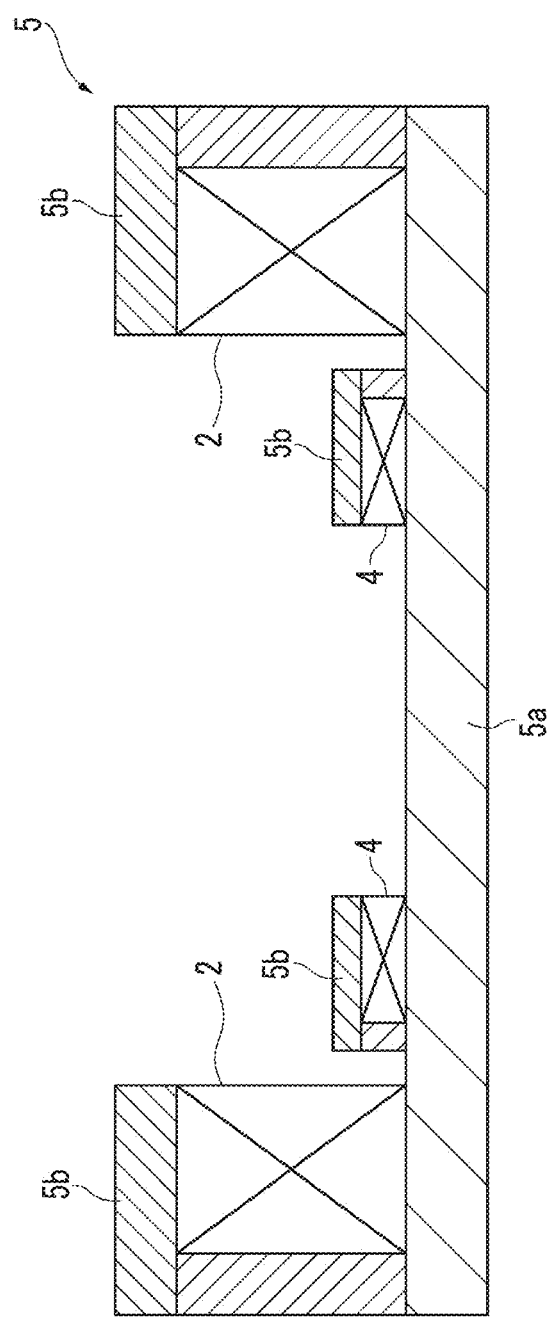
FIG. 5 is a sectional view taken along line V-V in FIG. 4.

As illustrated in FIGS. 4 and 5, the support unit 5 is configured to include a plate-shaped member 5a which is wide along the longitudinal direction of the main coil 2 and the correction coil 4, and a coil holding member 5b which is vertically disposed in the plate-shaped member 5a, which supports the main coil 2 and the correction coil 4 so as to be supported from outside, and which has an L-shaped cross section. The plate-shaped member 5a is disposed in the lateral direction across a region on the inner peripheral side of the main coil 2, and is disposed in the lateral direction across a region on the inner peripheral side of the correction coil 4. The coil holding member 5b is disposed so as to hold a position of opposing the main coil 2 from both sides and to hold a position of opposing the correction coil 4 from both sides.

Figure 6:
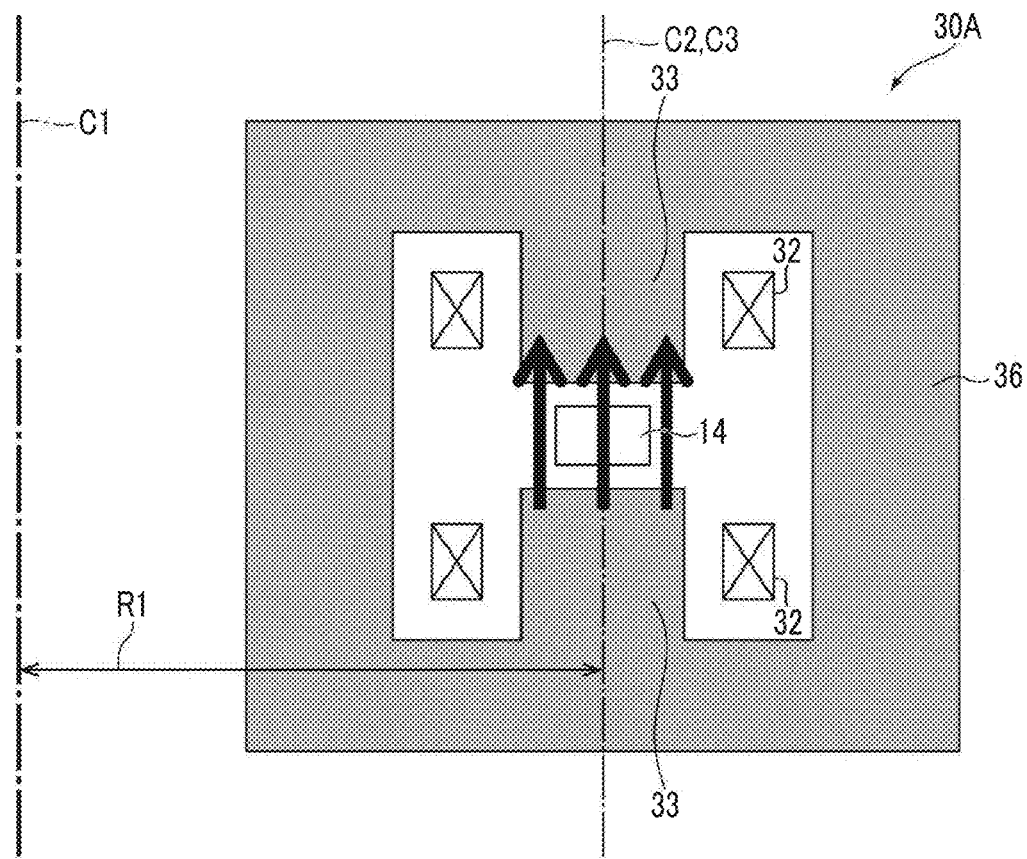
FIG. 6 is a schematic view illustrating a superconductive electromagnet according to a comparative example.
Figure 7:
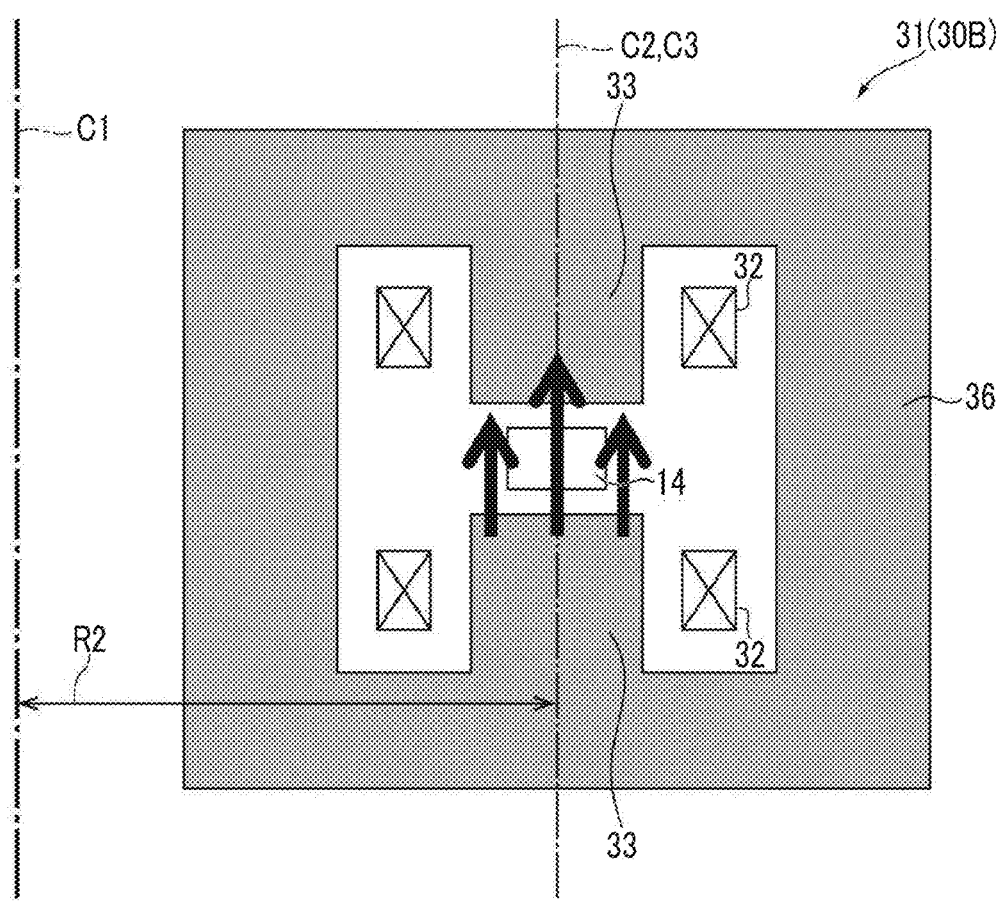
FIG. 7 is a schematic view illustrating a state where the superconductive electromagnet according to the comparative example causes magnetic saturation.

Here, referring to FIGS. 6 and 7, deflection electromagnets 30A and 30B according to a comparative example will be described. The deflection electromagnet 30A according to the comparative example is configured to include a general electromagnet other than the superconductive electromagnet. The deflection electromagnet 30A includes a pair of main coils 32 and 32 having an annular shape, a pair of magnetic poles 33 and 33 arranged on the inner peripheral side of the main coil 32, and the beam duct 14 disposed between a pair of the magnetic poles 33 and 33 so as to pass through the deflection electromagnet 30A. A pair of the magnetic poles 33 and 33 are configured to have a ferromagnetic material, and is formed integrally with a yoke 36 formed so as to surround the main coil 32.

For example, the deflection electromagnet 30A is used for a beam transport line applied to a rotary gantry of the charged particle beam therapy apparatus. In the beam transport line of the charged particle beam therapy apparatus, on a downstream side of a scanning electromagnet, a size of a beam duct is caused to increase in order to allow the charged particle beam used in scanning to pass therethrough. Here, in order to accurately deflect the charged particle beam, it is necessary to realize uniform density of a magnetic flux even in the size-increased beam duct. For this reason, it is necessary to increase a size of the deflection electromagnet.

It is known that when the charged particle beam is deflected by the deflection electromagnet 30A, a distance from a deflection center C1 of the charged particle beam to a track center C2 is inversely proportional to a size of the density of the magnetic flux in the beam duct 14 inside the deflection electromagnet 30A. In the deflection electromagnet according to the comparative example, in order to decrease a size of the electromagnet, it is necessary to shorten a distance R1 from the deflection center C1 of the charged particle beam to the track center C2. For this purpose, the density of the magnetic flux in the beam duct 14 may become higher. Therefore, as illustrated in FIG. 7, the deflection electromagnet 30B according to the comparative example is configured to have a superconductive electromagnet. In this manner, the density of the magnetic flux in the beam duct 14 can become higher, thereby further shortening a distance R2 from the deflection center C1 of the charged particle beam to the track center C2 than the distance R1.

However, since the deflection electromagnet 30B according to the comparative example is configured to have a superconductive electromagnet, a magnetomotive force is great. Accordingly, in some cases, the magnetic pole 33 arranged on the inner peripheral side of the main coil 32 causes magnetic saturation. In this case, there is a problem in that the density of the magnetic flux in the beam duct 14 inside the deflection electromagnet 30 becomes high near the axis C3 of the main coil 32 and thus uniformity in the density is degraded. FIGS. 6 and 7 illustrate the track center C2 of the charged particle beam and the axis C3 of the main coil 32 so as to overlap each other. In contrast, for example, it is also conceivable to realize uniform density of the magnetic flux by forming an irregular shape on an opposing surface of the magnetic poles 3 and 3. However, according to this method, an advantageous effect can be obtained for only the density of the magnetic flux having a specific size. According to this method, the uniform density of the magnetic flux cannot be maintained, if the density of the magnetic flux is changed due to a change in energy of the charged particle beam. Consequently, there is a problem in that the uniformity cannot be maintained for the density of the magnetic flux covering a wide range.

On the other hand, in the deflection electromagnet 20 employing the superconductive electromagnet 1 according to the embodiment described herein, a pair of the correction coils 4 and 4 are arranged between a pair of the magnetic poles 3 and 3 on the inner peripheral side of the main coils 2 and 2 having an annular shape. In this manner, the density of the magnetic flux generated by the main coils 2 and 2 is corrected by the density of the magnetic flux generated by the correction coils 4 and 4. Accordingly, it is possible to realize improved uniformity in the density of the magnetic flux in the beam duct 14 between the magnetic poles 3 and 3. That is, it is possible to realize the improved uniformity in the density of the magnetic flux between the magnetic poles 3 and 3 where deflection electromagnet 20 is enabled to cope with a change in the density of the magnetic flux covering a wide range by configuring the opposing surfaces 3a and 3a of the respective magnetic poles 3 and 3 so as to be planes respectively.

The deflection electromagnet 20 which is configured to have the superconductive electromagnet 1 and which deflects the charged particle beam includes at least a pair of the correction coils 4. In this manner, it is possible to realize more improved uniformity in the density of the magnetic flux in the beam duct 14 inside the deflection electromagnet 20.

In the deflection electromagnet 20 which is configured to have the superconductive electromagnet 1 and which deflects the charged particle beam, a width in the direction of axis C4 of the correction coil 4 is narrower than a width in a direction orthogonal to the direction of the axis C4 of the correction coil 4 in the cross section 4a perpendicular to the current flowing direction. In this manner, the density of the magnetic flux generated by the correction coil 4 can be concentrated on a narrow region. Therefore, it is possible to efficiently realize improved uniformity in the density of the magnetic flux in the beam duct 14 inside the deflection electromagnet 20.

The deflection electromagnet 20 which is configured to have the superconductive electromagnet 1 and which deflects the charged particle beam further includes the support unit 5 which supports the main coil 2 and supports the correction coil 4. In this manner, it is possible to support the correction coil 4 and to reinforce the main coil 2. Therefore, it is possible to prevent the main coil 2 from being deformed due to an extending force acting so as to extend the main coil 2 outward.

The charged particle beam therapy apparatus 100 has the above-described deflection electromagnet 20 which is configured to have the superconductive electromagnet 1 and deflects the charged particle beam. In this manner, the density of the magnetic flux generated by the main coil 2 is corrected by the density of the magnetic flux generated by the correction coil 4. Accordingly, it is possible to realize improved uniformity in the density of the magnetic flux in the beam duct 14 inside the deflection electromagnet 20 of the charged particle beam therapy apparatus 100.

The charged particle beam therapy apparatus 100 includes the deflection electromagnet 20 which deflects the charged particle beam, and the scanning electromagnet 21 which performs scanning by using the charged particle beam, and employs the above-described superconductive electromagnet 1 as the deflection electromagnet 20 disposed on the further downstream side of the charged particle beam from the scanning electromagnet 21. In this manner, even when the superconductive electromagnet 1 is employed as the deflection electromagnet 20 disposed on the downstream side of the scanning electromagnet 21, it is possible to realize improved uniformity in the density of the magnetic flux in the beam duct 14 inside the deflection electromagnet 20.

Certain embodiments of the present invention are not limited to the above-described embodiments. For example, in the above-described embodiments, the superconductive electromagnet 1 is applied to the deflection electromagnet 20 arranged in the rotary gantry 23 of the charged particle beam therapy apparatus 100. However, without being limited to the deflection electromagnet 20, the superconductive electromagnet 1 may be applied to other electromagnets such as the focusing electromagnet 19 or the scanning electromagnet 21. In addition, without being limited to the charged particle beam therapy apparatus 100, the superconductive electromagnet 1 may be applied to an apparatus having the beam transport line such as a cyclotron, for example.

In the above-described embodiments, the superconductive electromagnet 1 includes a pair of the main coils 2 and a pair of the correction coils 4, respectively. However, the superconductive electromagnet 1 may include only one of the main coils 2 or only one of the correction coils 4. Alternatively, the superconductive electromagnet 1 may include more main coils 2 or more correction coils 4. If the superconductive electromagnet 1 includes only one of the main coils 2 or only one of the correction coils 4, it is possible to further miniaturize the superconductive electromagnet 1. On the other hand, if the superconductive electromagnet 1 includes the main coils 2 or the correction coils 4 whose number is more than a pair, it is possible to realize more improved uniformity in the density of the magnetic flux in the beam duct 14 inside the deflection electromagnet 20.

According to the above-described embodiments, in order to negate a region where the density of the magnetic flux generated by the main coil 2 is particularly high, the power is supplied to the main coil 2 and the correction coil 4 so that currents reversely flow around the main coil 2 and the correction coil 4. However, in order to supplement a region where the density of the magnetic flux generated by the main coil 2 is particularly low, the power may be supplied to the main coil 2 and the correction coil 4 so that the currents flow in the same direction in the main coil 2 and the correction coil 4. Even in this case, it is possible to realize improved uniformity in the density of the magnetic flux in the beam duct 14 inside the deflection electromagnet 20.

According to the above-described embodiments, the support unit 5 is configured to include the plate-shaped member 5a which is wide along the longitudinal direction of the main coil 2 and the correction coil 4. However, the support unit 5 is not limited to this shape. That is, the support unit 5 may be configured to include a rod-shaped member which is narrow along the longitudinal direction of the main coil 2 and the correction coil 4. The examples illustrated in FIGS. 4 and 5 adopt a configuration in which a region on the inner peripheral side of the correction coil 4 is closed by the support unit 5. However, a configuration may be adopted in which the region on the inner peripheral side of the correction coil 4 is not closed by the support unit 5. Even in this case, the support unit 5 can support the correction coil 4 and can reinforce the main coil 2. Therefore, it is possible to prevent the main coil 2 from being deformed due to an extending force acting so as to extend the main coil 2 outward.

A high-temperature superconductive coil for forming the main coil 2 or the correction coil 4 may be a pancake coil made from a tape wire. In this case, it is possible to prevent performance from being degraded by the high-temperature superconductive coil being twisted.

As an electromagnet power source for supplying the power to the correction coil 4, multiple electromagnet power sources may be provided. Alternatively, winding density of the correction coil 4 may not be uniform. In any case, it is possible to arrange density distribution of the current inside the correction coil 4 so as not to be uniform. Therefore, it is possible to realize further improved uniformity in the density of the magnetic flux in the beam duct 14 inside the deflection electromagnet 20.

A device for measuring the density of the magnetic flux may be arranged in the beam transport line 13. Base on the measured density of the magnetic flux, an electromagnet power source for supplying the power to the correction coil 4 may perform feedback control on a current value for supplying the power to the correction coil 4. In this case, the correction coil 4 can generate the density of the magnetic flux having a proper size. Therefore, it is possible to realize further improved uniformity in the density of the magnetic flux in the beam duct 14 inside the deflection electromagnet 20.

It should be understood that the invention is not limited to the above-described embodiment, but may be modified into various forms on the basis of the spirit of the invention. Additionally, the modifications are included in the scope of the invention.

What is claimed is:

1. A superconductive electromagnet comprising:
   a main coil that has an annular shape;
   a pair of magnetic poles that respectively have opposing surfaces which are planes opposing each other while being separated from each other in an axial direction of the main coil, and that are arranged on an inner peripheral side of the main coil; and a correction coil that is arranged between the pair of magnetic poles,
wherein a non-uniform width of a density of magnetic flux after being corrected by the correction coil is narrower than a non-uniform width of a density of magnetic flux generated by the main coil.

2. The superconductive electromagnet according to claim 1, wherein at least a pair of the correction coils is provided.

3. The superconductive electromagnet according to claim 2,
wherein a non-uniform width of a density of magnetic flux after being corrected by each of the pair of the correction coils is narrower than the non-uniform width of the density of magnetic flux generated by the main coil.

4. The superconductive electromagnet according to claim 1,
wherein the correction coil is configured so that a width in the axial direction of the correction coil is narrower than a width in a direction orthogonal to the axial direction of the correction coil, in a cross section perpendicular to a current flowing direction.

5. A charged particle beam therapy apparatus comprising: the superconductive electromagnet according to claim 1.

6. The charged particle beam therapy apparatus according to claim 5, further comprising:
a deflection electromagnet that deflects a charged particle beam; and
a scanning electromagnet that performs scanning by using the charged particle beam,
wherein the superconductive electromagnet is used as the deflection electromagnet which is disposed on a further downstream side of the charged particle beam from the scanning electromagnet.

7. The superconductive electromagnet according to claim 1,
wherein the correction coil has an annular shape, and
wherein a current around the correction coil flows in a reverse direction compared to a current around the main coil.

* * * * *